Figure 1:
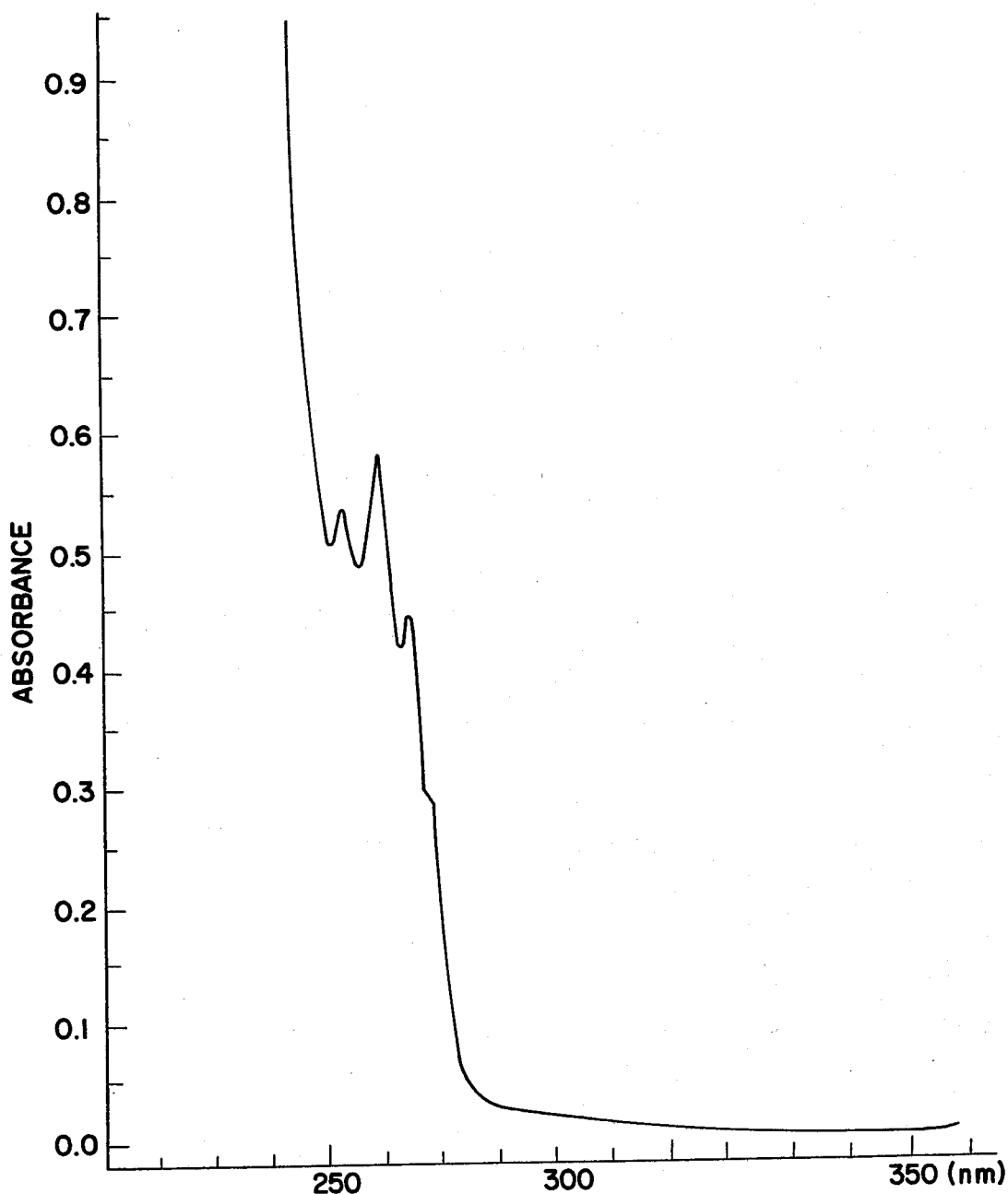

United States Patent [19]

Takemoto et al.

[11] 4,452,782

[45] Jun. 5, 1984

[54] PENTADECAPEPTIDE

[75] Inventors: Kenji Takemoto, Fujisawa; Yumiko Miyasaka, Yokohama; Hideo Ishitsuka, Yokohama; Yasuji Suhara, Yokohama; Hiromi Maruyama, Yokohama, all of Japan

[73] Assignee: Hoffmann-La Roche Inc., Nutley, N.J.

[21] Appl. No.: 411,742

[22] Filed: Aug. 26, 1982

Related U.S. Application Data

[63] Continuation of Ser. No. 255,578, Apr. 20, 1981, abandoned, which is a continuation-in-part of Ser. No. 132,370, Mar. 21, 1980, abandoned.

[30] Foreign Application Priority Data

Apr. 2, 1979 [GB] United Kingdom ................. 7911395

[51] Int. Cl.$^3$ ..................... A61K 37/02; C07C 103/52
[52] U.S. Cl. ............................... 424/177; 260/112.5 R
[58] Field of Search ..................... 424/177; 260/112 R, 260/112.5 R

[56] References Cited

PUBLICATIONS

Hadfield, A., *Antibiotics & Chemotherapy*, 2(11), 1952, p. 590.

Benedict, R. et al., *Antibiotics & Chemotherapy*, 2(11), 1952, pp. 591–594.

Dronch, W. et al., *Antibiotics & Chemotherapy*, 4(11), 1954, pp. 1135–1142.

Weinstein, M. et al., *J. of Chromatography*, 15; 1978, pp. 415–463.

Isaaq, H. et al., *J. of Chromatography*, 133, 1977, pp. 291–301.

*Primary Examiner*—Delbert R. Phillips
*Assistant Examiner*—F. T. Moezie
*Attorney, Agent, or Firm*—Jon S. Saxe; Bernard S. Leon; Frank P. Hoffman

[57] ABSTRACT

A pentadecapeptide and salts thereof with immunopotentiating activity is presented. Also presented is a fermentation process for the preparation of the pentadecapeptide by a microorganism of the genus Streptoverticillium and pharmaceutical preparations containing the peptide or its salts.

3 Claims, 4 Drawing Figures

PENTADECAPEPTIDE

This is a continuation, of application Ser. No. 255,578 filed Apr. 20, 1981, which is a continuation-in-part of U.S. Ser. No. 132,370, filed Mar. 21, 1980, now abandoned.

DESCRIPTION OF THE INVENTION

The present invention relates to a novel pentadecapeptide and to salts thereof. The invention also relates to a process for the manufacture of the novel compounds, to pharmaceutical preparations containing them and to the use of the pentadecapeptide and its salts as immunopotentiating agents.

The novel pentadecapeptide provided by the present invention is a white powder containing the following amino acids: arginine (1 mole), glutamic acid* (1 mole), lanthionine (1 mole), β-methyllanthionine (2 moles), D-phenylalanine (3 moles), glycine (2moles), proline (1 mole), valine (1 mole), aspartic acid* (1 mole), β-hydroxyaspartic acid* (1 mole), and lysinoalanine (1 mole).

The asterisks are meant to indicate that either two of these amino acids or one of them and the carboxy terminal amino acid are present as amides.

Figure 2:
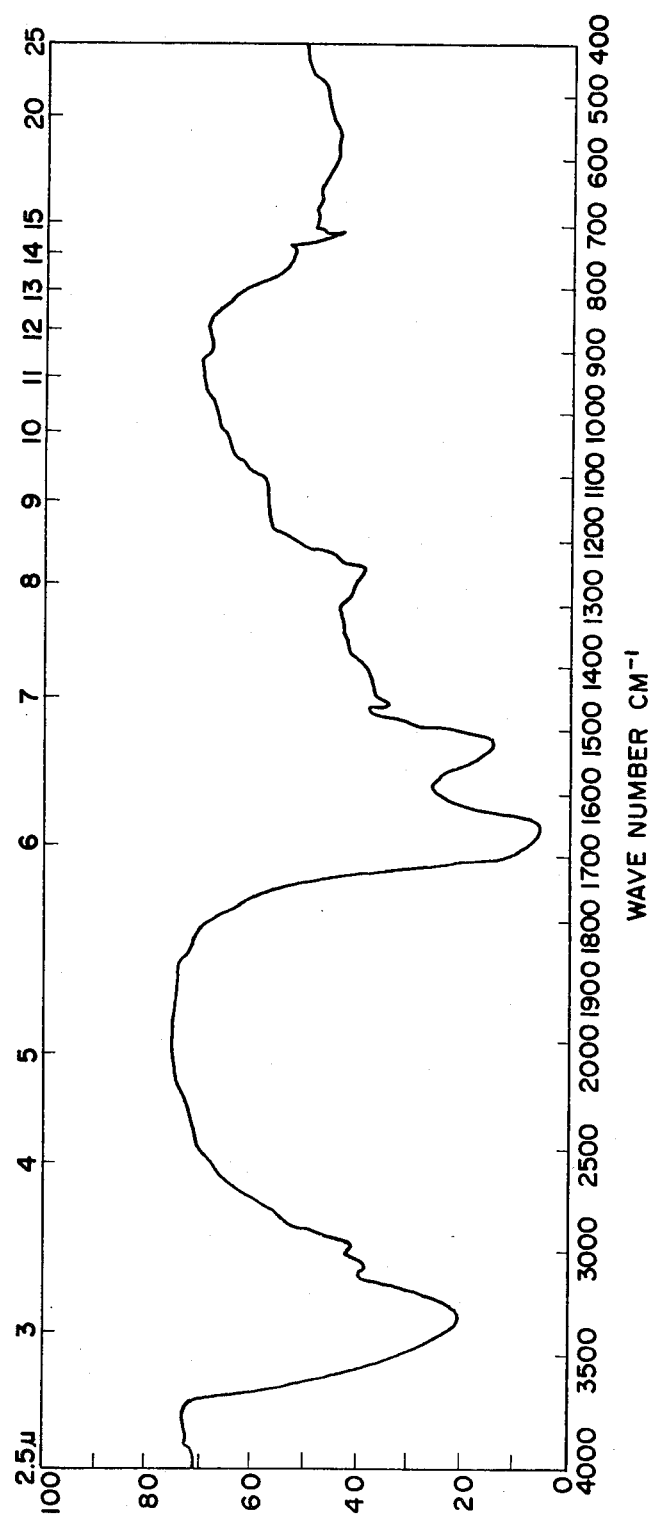

The pentadecapeptide hydrochloride is characterized by the following physicochemical data:

(a) Melting point: 257°–259° C. (dec.)
(b) Specific rotation: $[\alpha]_D^{25} = -72°$ (c=1.0, 0.1N HCl)
(c) Ultraviolet absorption spectrum:
Maxima at 251.5 nm ($E_{1cm}^{1\%}=2.68$), 257 nm ($E_{1cm}^{1\%}=2.90$) and 263 nm ($E_{1cm}^{1\%}=2.29$), shoulder at 266 nm in water. The spectrum is shown in FIG. 1.
(d) Infrared absorption spectrum:
The spectrum in a KBr pellet is shown in FIG. 2.
(e) Solubility in solvents:
The salt is soluble in water or methanol, hardly soluble in ethyl acetate, and insoluble in hexane.
(f) Color reaction:
The salt is positive to Sakaguchi and Reidon-Smith reactions, and negative to Pauly reaction.
(g) Thin layer chromatography on silica gel $F_{254}$ (Merck) in benzene/ethanol/25% aqueous ammonia (2:4:1, v/v/v): Rf=0.4.

According to the present invention the pentadecapeptide is produced by a process which comprises cultivating a microorganism belonging to the genus Streptoverticillium, capable of producing such pentadecapeptide, under aerobic conditions in an aqueous medium, isolating the peptide from the fermentation broth and, if desired, forming a salt thereof.

The pentadecapeptide-producing microorganisms used according to the present invention include all strains belonging to the genus Streptoverticillium which are capable of producing this peptide, including mutants and variants thereof. A preferred strain thereof is Streptoverticillium griseoverticillatum NAR 164C-MY6 which was isolated from soil in Sydney, Australia, including subcultures, mutants and variants thereof.

The strain, Streptoverticillium griseoverticillatum NAR 164C-MY6, has been deposited in the Agency of Industrial Science and Technology, Fermentation Research Institute, Japan, under "FERM-P No. 4639" on Aug. 31, 1978 and at the American Type Culture Collection under No. 31499 on Mar. 13, 1979 and is part of the present invention. The mycological characteristics thereof are as follows:

I. Morphology

The said strain develops aerial mycelium from abundantly grown substrate mycelium on several ISP agar media. The aerial mycelia formed mainly biverticillate whirls with the minority being monoverticillate. Spiral formation was not recognized. Mature spore chains contained about 10 spores per chain. The spore was of 0.4–0.6×0.8–1.2μ in diameter, oval to cylindrical in shape and its surface was smooth.

II. Cultural characteristics

The strain NAR 164C-MY6 (FERM-P No. 4639, ATCC No. 31499) has the cultural characteristics as mentioned in Table 1 below. The tests were carried out using standard media for Streptomyces defined by International Streptomyces Projects (Shirling, E. B. & D. Gottlieb: "Methods for Characterization of Streptomyces Species," Int. J. Syst. Bact. 16, No. 3, pages 313–340, 1966) and by Waksman (Waksman, S.A.: "The Actinomycetes," Vol. 2, The Williams & Wilkins Co., Baltimore, 1961). Each culture was incubated at 27° C. for 3–21 days except that the skim milk test was performed at 37° C. Color determinations were made according to the Color Harmony Manual, 4th ed. 1958 (Container Cooperation of America, Chicago).

As indicated in Table 1, the color of the substrate mycelia was pale yellowish brown to yellowish brown and that of the aerial mycelia was pale pink to grayish yellowish pink on several media. Soluble pigment was not formed.

TABLE 1

Cultural characteristics of the strain NAR164C-MY6 (FERM-P No. 4639)

| Test items | | Results or observation on NAR164C-MY6 |
|---|---|---|
| Sucrose-nitrate agar | A-M | Thin, Pale pink [4ca, Flesh Pink] |
| | G | Colorless~Yellowish gray [3ba, Pearl] |
| | S-P | — |
| Glucose-asparagine agar | A-M | Thin, Yellowish gray [3ba, Pearl] |
| | G | Pale yellowish brown [2ic, Honey Gold~21e, Mustard] |
| | S-P | — |
| Glycerol-asparagine agar [ISP medium - 5] | A-M | Good, Brownish white [2ba, Pearl]~Pale yellowish orange [3ca, Shell] |
| | G | Colorless~Pale yellow [2ca, Lt. Ivory] |
| | S-P | — |
| Inorganic slat-starch agar [ISP medium - 4] | A-M | Good, Pinkish white [5ba, Shell Pink]~Pale reddish brown [4gc, Rose Beige] |
| | G | Pale yellowish brown [2ic, Honey Gold]~Yellowish brown [3ne, Topaz] |
| | S-P | — |

TABLE 1-continued
Cultural characteristics of the strain NAR164C-MY6 (FERM-P No. 4639)

| Test items | | Results or observation on NAR164C-MY6 |
|---|---|---|
| Tyrosine agar [ISP medium - 7] | A-M | Good, Pale orange [3cb, Sand]~Grayish yellowish pink [4ec, Lt Rose Beige] |
| | G | Pale yellowish brown [21e, Mustard ~ 2gc, Bamboo] |
| | S-P | — |
| Nutrient agar | A-M | Thin, Brownish white [2ba, Pearl] |
| | G | Pale yellowish brown [2gc, Bamboo]~ yellowish brown [3ng, Yellow Maple] |
| | S-P | — |
| Yeast extract-malt extract agar [ISP medium - 2] | A-M | Moderate~Good, White~Pale orange [3cb, Sand] |
| | G | Pale yellowish brown [2gc, Bamboo] |
| | S-P | — |
| Oatmeal agar [ISP medium - 3] | A-M | Good, Pale pink [4ca, Flesh Pink]~ Grayish yellowish pink [4ec, Lt Rose Beige] |
| | G | Pale yellow [2ca, Lt Ivory]~Light brownish gray [2ec, Sand] |
| | S-P | — |
| 10% skim milk-nutrient agar | A-M | Thin, White |
| | G | Colorless |
| | S-P | — |
| 10% skim milk (37° C.) | A-M | Thin, White |
| | G | Colorless~Pale yellow |
| | S-P | — |
| Glucose-peptone gelatin | A-M | — |
| | G | Colorless |
| | S-P | — |

A-M: aerial mycelium
G: substrate mycelium
S-P: soluble pigment

III. Physiological properties (1) Temperature range of growth:
The results tested on ISP medium-2 were as follows:

| Temperature | 10° C. | 24° C. | 27° C. | 32° C. | 37° C. | 45° C. |
|---|---|---|---|---|---|---|
| Growth | − | + | + | ++ | ++ | − |

Growth was not observed at 10° C. and 45° C. The optimal temperature for growth was found at around 32° C.–37° C.

(2) Gelatin liquefaction on glucose-peptone-gelatin cultured at 27° C.:
The liquefaction was positive after the 10th day and its intensity was strong.

(3) Starch hydrolysis on inorganic salts-starch agar cultured at 27° C.:
The hydrolysis was positive but medium in its intensity.

(4) Coagulation and peptonization in 10% skim milk medium at 37° C.:
The coagulation became positive on the 4th day and completed on the 7th day. After that, the peptonization became positive. The intensity of the coagulation was strong, but that of the peptonization was medium.

(5) Casein hydrolysis on 10% skimmed milk-nutrient agar at 27° C.
The hydrolysis was positive with medium intensity.

(6) Formation of melanin-like pigment at 27° C.:
No pigment was formed on trypton-yeast broth (ISP-1); peptone-yeast-iron agar (ISP-6); and tyrosine agar (ISP-7).

IV. Utilization of carbohydrates on Pridham-Gottleib agar medium (ISP-9) cultured at 27° C.

A good growth was observed only with glucose and inositol as the sole carbon source. L-Arabinose, D-xylose, D-fructose, sucrose, rhamnose, raffinose and D-mannitol were not utilized.

When all the above biological properties were investigated in the light of species described in ISP reports (Shirling, E. B. & D. Gottleib: Cooperative description of type cultures of Streptomyces, Int. J. Syst. Bact., 18, Nos. 2 & 4, 1968; 19, No. 4, 1969; 22, No. 4 1972), Waksman (Waksman, S. A.: The Actinomycetes, Vol. 2, The Williams & Wilkins Co., Baltimore, 1961) and Bergey's Manual (Robert, S., E. G. Breed, D. Murray & N. R. Smith: Bergey's Manual of Determinative Bacteriology, 7th ed., Williams & Wilkins Co., Baltimore, 1957: Buchanan, R. E. & N. E. Gibbons: Bergey's Manual of Determinative Bacteriology, 8th ed., Williams & Wilkins Co., Baltimore, 1974), the strain NAR164C-MY6 was found to be closely related to Streptoverticillium hachijoensis (Int. J. Syst. Bact., 18, p. 128, 1968; The Actinomycetes, Vol. 2, pp. 226–227, 1961; Bergey's Manual of Determinative Bacteriology, pp. 837–838, 1974; Yamaguchi, T., Studies on the antibiotic substance-producing strains H-2075, H-2609 (S. hachijoensis nov. sp.) and H-3030, J. Antibiotics, Tokyo, Ser. A, 7, 10–14, 1954) and Streptoverticillium griseoverticillatum (Int. J. Syst. Bact., 22, p. 306, 1972; Bergey's Manual of Determinative Bacteriology, 8th ed., p. 840, 1974; Shinobu, R. & Y. Shimada, On a new whirl-forming species of Streptomyces, Bot. Mag. Tokyo, 75, 170–175, 1962). Thus, a comparative study by the parallel culture was undertaken with Sv. hachijoensis ISP 5114 and Sv. griseoverticillatum ISP 5507, the results of which are summarized in Table 2.

TABLE 2

Comparison of strain NAR164C-MY6 (FERM-P No. 4639) with
*Streptoverticillium hachijoensis* ISP 5114 and *Sv.
griseoverticillatum* ISP 5507.

| Tests | NAR164C-MY6 (FERM-P No. 4639) | Sv. hachijoensis ISP 5114 | Sv. grisco-verticillatum ISP 5507 |
|---|---|---|---|
| Morphology on ISP agar media | Mainly biverticillate, minor monoverticillate | Monoverticillate & biverticillate | Mainly biverticillate, minor monoverticillate |
| ISP medium - 3 | | | |
| A-M | Pale pink~Grayish yellowish pink | Pale pink~Pale yellowish orange | Pale orange~Grayish yellowish pink |
| R* | Light brownish gray~Yellowish brown | Pale yellow~Dull yellow | Pale yellowish Brown~Yellowish brown |
| S-P | — | Faint yellow | — |
| Melanine pigment | | | |
| ISP medium - 6 | — | — | — |
| ISP medium - 7 | — | — | — |
| ISP medium - 1 | — | — | — |
| Skimmed milk | | | |
| Coagulation | ++ | ++ | ++ |
| Peptonization | + | + | + |
| Gelatin liquefaction | ++ | ++ | — (probably) |
| Starch hydrolysis | + | + | + |
| Casein hydrolysis | + | + | + |
| Optimum temperature | 32°~37° C. | 32°~37° C. | 32°~37° C. |
| Utilization of | | | |
| L-Arabinose | — | — | — |
| D-Xylose | — | — | — |
| Glucose | ++ | ++ | ++ |
| D-Fructose | — | — | — |
| Sucrose | — | — | — |
| Inositol | + | + | + |
| Rhamnose | — | — | — |
| Raffinose | — | — | — |
| D-Mannitol | — | — | — |

++ = strong positive, + = positive, — = negative, R* = Reverse side color

The strain NAR164C-MY6 differs distinctly from ISP 5114 in that the latter strain forms little whirl on ISP 9 plus glucose medium, forms exclusively monoverticillate whirl on ISP 2 medium and shows clear yellow color in the reverse side when grown on ISP media 3, 4 and 5, together with the production of soluble pigment to color in faint yellow.

On the other hand, the said strain seems to resemble very closely ISP 5507 strain, although some differences were observed both morphologically and physiologically as follows: ISP 5507 shows vervetty formation of aerial mycelia, while that of NAR164C-MY6 is cottony. NAR164C-MY6 liquefies gelatin strongly, while ISP 5507 can be judged probably negative, although it was reported in the above original paper positive. However, these differences are small in balance with their great similarities in morphology, color of the reverse, pigment formation and so forth. In view of the above different properties, this taxon was named Streptoverticillium griseoverticillatum NAR 164C-MY6.

The cultivation may be carried out in a culture medium containing conventional nutrient substances which the microorganism used in the present invention can utilize. The carbon sources, for example, are starch, glucose, molasses or a mixture thereof; and the nitrogen sources, for example, are soybean powder, meat extract, peptone, corn steep liquor, yeast extract, ammonium sulfate, sodium nitrate, ammonium chloride or a mixture thereof. Furthermore, if necessary, the culture medium may contain suitable inorganic substances such as calcium carbonate, sodium chloride and the like; and/or salts of zinc, copper, manganese, iron and the like. In addition, an antifoaming agent such as silicone, vegetable oil and the like may also be added to the culture medium in order to prevent foaming during the cultivation.

The cultivation in accordance with the present invention is effected under aerobic conditions in an aqueous medium, especially by a submerged fermentation process. The pH of the medium at the beginning of the cultivation is about 7. The preferred temperature for the cultivation is in the range of 20°-40° C., most preferably 25°-30° C.

When the cultivation is carried out for about 1-5 days, under the conditions mentioned above, the pentadecapeptide can be conveniently obtained in the fermentation broth. The cultivation is suitably terminated at the time when the maximum potency of the pentadecapeptide has been attained.

The amount of pentadecapeptide obtained is determined by the following method:

The pentadecapeptide has an antibacterial activity against Bacillus subtilis PCI 219 in addition to an immunostimulating activity. Therefore, it can be determined by a conventional antibiotic assay method such as a cylinderplate or paper-disc method using said bacteria as a tester strain. According to said antibiotic assay method, the amount of peptide produced during the fermentation can be determined. Furthermore, the purification steps can also be monitored by said assay.

After the cultivation, the isolation and purification of the peptide produced in the fermentation broth can be effected by using methods known per se such as the following:

From the fermentation broth obtained by the aforementioned manner, the mycelia are removed by centrifugation or filtration. Purification of the pentadecapeptide can be carried out by means of chromatography such as adsorption, ion exchange or dextran gel chromatography.

A preferred embodiment is as follows: The pH of the fermentation broth containing the pentadecapeptide is adjusted to 4-5. The fermentation broth is filtered to remove the mycelia. The filtrate is then passed through a column of a weakly acidic cation exchange resin, such as Amberlite IRC-50 (H-form) to adsorb the peptide. The column is washed with water and eluted with a mixture of 0.5N hydrochloric acid and acetone (1:1, v/v). The eluate is neutralized and concentrated, whereby the crude peptide is precipitated. The precipitate is collected by filtration and dissolved in acidic water to remove insoluble impurities. The solution is adjusted to pH 7-8 and extracted with a solvent such as n-butanol. Alternatively, the aforementioned concentrate may be directly extracted with the solvent. The solvent is removed from the extract to obtain the peptide as a crude powder. The crude powder is dissolved in water and passed through a column of an absorbent such as SP-Sephadex to adsorb the peptide. The column is washed with 0.01 M sodium chloride and then eluted with 0.01 M-0.05 M sodium chloride by turns. The fractions containing the peptide are concentrated and adjusted to pH 3.8-4.0. The concentrate is passed through a column of active carbon. The column is washed with water and eluted with 50% aqueous acetone. The eluate is concentrated, the concentrate allowed to stand at room temperature and the precipitated crystalline substance is filtered to obtain the pure peptide. If desired, it can be converted into various salts such as the hydrochloride, sulfate, phosphate, oxalate and the like using methods well known in the art.

The pentadecapeptide thus obtained is characterized as above.

There have hitherto been reported the following substances which are similar to the present pentadecapeptide but are clearly distinguishable therefrom:
Leucopeptin (J. Antibiotics Ser. A 17, 262, 1964);
Leucinamycin (J. Antibiotics Ser. A 20, 194, 1967);
Cinnamycin (Antibiotics and Chemotherapy 4, 1135, 1954);
KM-8 (J. Antiobitics 28, 819, 1975);
Duramycin (Proceedings of the 14th European Peptide Symposium pp. 183-191, 1976); and
Arsimycin (German Pat. No. 1,090,380).

Leucopeptin, KM-8 and Duramycin differ from the present peptide in that they contain lysine. Leucinamycin and Arsimycin contain leucine and cystine respectively, while Cinnamycin does not contain glycine.

Biological activity of the pentadecapeptide

The pentadecapeptide was found to induce the release of an interferon-like substance in mouse spleen cell cultures and exhibits a thymic hormone-like activity.

(1) Induction of an interferon-like activity

Figure 3:
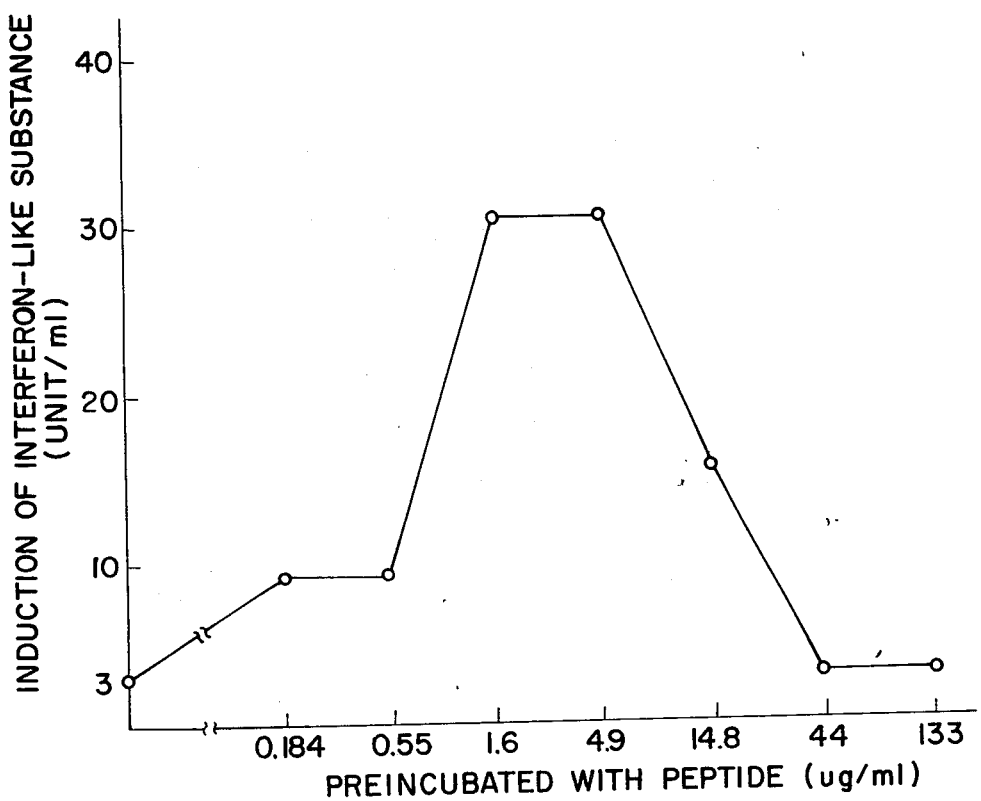

Spleen cells from C57BL/6 mice in a single cell suspension ($1 \times 10^7$ cells/ml) were taken up in a medium RPMI1640 supplemented with 5% fetal bovine serum and 10 mM Hepes buffer (pH 7.3). They were cultured for 2 hrs. with the serially diluted pentadecapeptide and for another 4 hrs. after washing out of the peptide. The supernatants were assayed for their interferon-like activity. The results are given in FIG. 3.

(2) Enhancement of cell-mediated immunity

The pentadecapeptide was examined for its activity in cell-mediated immunity by employing the delayed type hypersensitivity (DTH) reaction against sheep red blood cell (SRBC) in mice.

Male CDF$_1$ mice (22-25 g, 9 weeks old) were immunized by injection of $10^8$ SRBC in 0.05 ml saline into right hind footpad. Four days later, the DTH reaction was elicited by injection of $10^8$ SRBC into the left hind footpad and difference in thickness between untreated right and antigen injected left footpad was measured with a carpenter's caliper 24 hrs. later. The pentadecapeptide was administered by a single p.o. injection at the dose of 1 mg or 100 µg at day 0 or day 4. As shown in Table 3, the swelling of the footpad treated with 1 mg of the peptide was increased by 40-50% compared with that of control mice, indicating that the peptide enhanced cell-mediated immunity to SRBC.

(3) Thymosin-like activity

The peptide was examined for its thymic hormone-like activity by the E-rosette assay method using azathiopurine and was compared with thymosin fraction 5.

Spleen cells from athymic mice (Balb/c, nu/nu) were incubated for 30 min. at 37° C. with MEM containing 5% calf serum, to which was added the sample to be tested. Azathiopurine was then added at a concentration of 8 µg/ml. After 60 min. of incubation at 37° C. SRBC were added and cell suspension was centrifuged. After standing at 4° C. for 60 min., wet cell preparations were examined by microscopy and the number of lymphocytes binding four or more SRBC (E-rosette forming cell, RFC) was counted. As shown in Table 4, the incubation with thymosin reduced the number of RFC, indicating that thymosin altered azathiopurine resistant RFC to be sensitive as the result of the differentiation of the splenocyte of athymic mice. The peptide showed the same activity as did thymosin, suggesting that it has thymosin-like activity at lower concentrations.

(4) Antitumor activity

Figure 4:
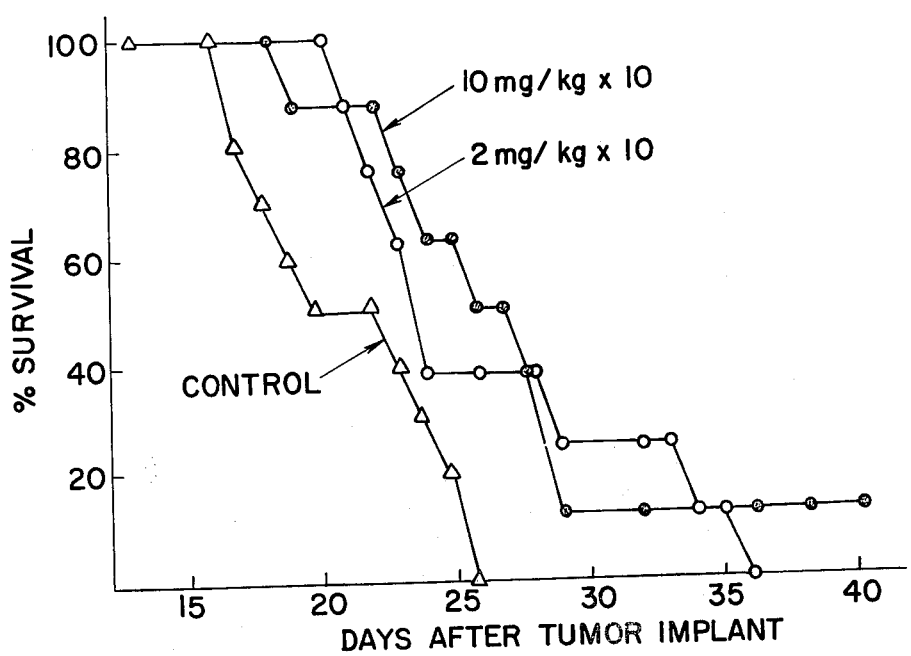

Since the pentadecapeptide could activate lymphocytes as mentioned above, it was expected to reveal an antitumor activity. The examination thus attempted for its antitumor activity against a syngeneic tumor, B16 mouse melanoma, has shown the positive effect in retarding the tumor (FIG. 4).

Male BDF$_1$ mice (5 weeks old) were subcutaneously implanted at day 0 with $10^6$ of B16 malanoma cells. The peptide was daily administered p.o. for 10 successive days from day 2.

In Table 5, the antitumor effect of the pentadecapeptide on growth of B16 melanoma is shown. Male C57BL/6 mice (6.5 weeks old) were subcutaneously implanted with $2 \times 10^5$ tissue culture cells of B16 melanoma. Then the mice were treated 15 times daily with the peptide from 24 hours later. At day 24 tumor volume was calculated. The peptide exhibited the activity to inhibit the tumor growth by 50-60% with 0.05-5 mg/kg daily for 15 times by oral route.

The antitumor activity of the peptide is further demonstrated in Table 6, 7 and 8 against Lewis lung carcinoma. In the experiment shown in Table 6, BDF$_1$ (C57BL/6×DBA/2) mice implanted with the tumor cells ($10^6$, sc) were treated daily for 15 times with the peptide from 24 hours later. The peptide inhibited the growth of the tumor by about 60% with 0.5 mg/kg/day by oral route.

The major problem in the treatment of cancer patient after surgical elimination of tumor is the prevention of metastasis of the tumor. Therefore, peptide was examined for its activity against the tumor system where an experimental design similar to clinical situation was devised.

Lewis lung carcinoma ($1\times10^6$) was implanted into footpad and at day 10 the advanced tumor was excised by amputation of the leg with the tumor developed. Then the mice were treated with cyclophosphamide (50 mg/kg, i.p.) 24 hrs later and at day 27 the dry weight of the tumor metastasized to lung was measured.

As shown in Table 7, when the mice were treated daily for 10 successive days with peptide after the amputation, the growth of the tumor metastasized was suppressed to about 45%.

On the other hand, the effect of the peptide on survival of the mice, which were amputated the advanced tumor and treated with cyclophosphamide, was examined. The experimental conditions were identical to the above experiment except that the advanced tumor was excised at day 12 and the mice were treated with cyclophosphamide at day 13. As shown in Table 8 the peptide prolonged clearly the survival days at doses of 0.5 and 0.05 mg/kg, daily for 15 times from day 13 to 27 by oral route.

(5) Suppression of bacterial infection

Since immunosurveillance systems are also known to be concerned in prevention of microbial infections, peptide was tested for its suppressive effect against a bacterial infection in mice. Male mice (ddy) weighing 25 g (6-weeks old) were infected intravenously with $1\times10^3$ of Listeria monocytogenes ATCC 15313. At 1, 2 and 4 days after infection, the number of the bacteria existed in liver, where the bacteria grow mainly, was counted. As shown in Table 9, when the mice were pretreated orally with peptide (0.05 mg/kg/day) for 10 successive days before the infection, the growth of the bacteria was suppressed to $10^{-3}$ level.

This effect of the peptide was also observed against *E. coli* 5A428-1E, *Pseudomonas aeruginosa* 5E81-1, and *Candida albicans* ATCC10231 (Table 10). Since the peptide did not have any in vitro activity against above organisms even at 100 μg/ml, these effects may be due to its immunological activity.

The effect was further extended against microbial infections in mice immunosuppressed by treatment of a cytostatic. Mice pretreated daily for 10 times with 5-fluorouracil (25 mg/kg/day, i.p.) were infected by either *Ps. aeruginosa* or *C. albicans* and the survivals were recorded on day 15. As shown in Table 11, pretreatment with the peptide is active against lethal infections at doses of 0.005 and 0.05 mg/kg/day by oral route.

These effects of the peptide would be a merit for prevention of opportunistic infection in compromised host.

TABLE 3

Enhancement of delayed-type hypersensitivity to SRBC by the pentadecapeptide in male $CDF_1$ mice

| Immunization | Eliciting injection | Thickness of footpad* $\times$ 0.1 mm | (% of control) |
|---|---|---|---|
| $10^8$ SRBC | $10^8$ SRBC | 4.6 ± 0.7 | (100) |

TABLE 3-continued

Enhancement of delayed-type hypersensitivity to SRBC by the pentadecapeptide in male $CDF_1$ mice

| Immunization | Eliciting injection | Thickness of footpad* $\times$ 0.1 mm | (% of control) |
|---|---|---|---|
| (control) $10^8$ SRBC peptide 1 mg/p.o. | $10^8$ SRBC | 6.7 ± 1.5** | (146) |
| $10^8$ SRBC peptide 0.1 mg/p.o. | $10^8$ SRBC | 5.3 ± 1.5 | (116) |
| $10^8$ SRBC | $10^8$ SRBC peptide 1 mg/p.o. | 6.3 ± 1.5** | (138) |
| $10^8$ SRBC | $10^8$ SRBC peptide 0.1 mg/p.o. | 5.0 ± 1.4 | (109) |

*Each value is the average of 6 mice together with S.E.
**P at least <0.01, compared with that of control.

TABLE 4

The alteration of roset forming cells of nu/nu mouse spleen from azathiopurine resistant to sensitive by peptide and thymosin fraction 5

| | azathiopurine resistant rosette forming cells/$10^6$ spleen cells | | |
|---|---|---|---|
| Sample | No. 1 | No. 2 | No. 3 |
| control | 758 | 535 | 1,005 |
| thymosin fraction 5 5 μg/ml | 393 | 309 | 679 |
| peptide | | | |
| 1 μg/ml | 590 | | |
| 0.1 | 562 | 453 | 924 |
| 0.033 | 507 | 350 | 815 |
| 0.01 | 421 | 309 | 679 |
| 0.001 | | 412 | 788 |
| 0.0001 | | 431 | 870 |

TABLE 5

Inhibition of growth of B16 melanoma

| Administration dose (mg/kg/day)/route | | Tumor growth ($cm^3$) at day 24 | No. of mice tested |
|---|---|---|---|
| none | | 4.30 ± 1.29 | 14 |
| peptide | 5/p.o. $\times$ 15 | 2.21 ± 0.61 | 10 |
| | 0.5 | 1.51 ± 0.74 | 9 |
| | 0.05 | 2.10 ± 0.39 | 10 |
| | 0.005 | 3.05 ± 1.21 | 10 |

TABLE 6

Inhibition of growth of Lewis lung carcinoma

| Administration dose (mg/kg/day)/route | | Tumor growth ($cm^3$) at day 16 | No. of mice tested |
|---|---|---|---|
| one | | 2.98 ± 1.34 | 20 |
| peptide | 5/p.o. $\times$ 15 | 1.66 ± 0.65 | 12 |
| | 0.5 | 1.46 ± 0.37 | 12 |
| | 0.05 | 1.97 ± 1.10 | 12 |
| | 0.005 | 2.47 ± 0.85 | 11 |
| | 0.005 | 3.16 ± 1.24 | 11 |

TABLE 7

Suppression of growth of Lewis lung carcinoma metastasized to lung in mice

| Administration dose (mg/kg/day)/route | dry weight of the tumor metastasized (mg ± S.D.) | No. of mice tested |
|---|---|---|
| Cyclophosphamide (CY) 50/ip $\times$ 1 | 45.9 ± 30.6 | 10 |
| + peptide 5/po $\times$ 10 | 22.9 ± 16.5 | 9 |

TABLE 7-continued

Suppression of growth of Lewis lung carcinoma metastasized to lung in mice

| Administration dose (mg/kg/day)/route | dry weight of the tumor metastasized (mg ± S.D.) | No. of mice tested |
|---|---|---|
| + peptide 0.5/po × 10 | 21.7 ± 16.7* | 10 |
| + peptide 0.05/po × 10 | 20.7 ± 19.4* | 10 |

*P < 0.05 when compared to CY alone

TABLE 8

Antitumor activity against Lewis lung carcinoma in combination with cyclophosphamide and surgery

| Administration dose (mg/kg/day)/route | Mean* survival days | Survivals at day 100 |
|---|---|---|
| Cyclophosphamide 50/i.p. × 1 | 32.6 ± 3.2 | 2/12 |
| Cyclophosphamide 50/i.p. × 1 + peptide 0.5/p.o. × 15 | 39.0 ± 5.9 | 9/12 |
| + peptide 0.5/p.o. × 15 | 37.5 ± 5.2 | 6/12 |

*Days after tumor implantation.

TABLE 9

Suppression of bacterial growth by peptide

| Days after infection | Growth of Listeria monocytogenes ($\log_{10}$ No. of bacteria/liver) | |
|---|---|---|
| | Control mice | Mice treated with peptide |
| 1 | 6.5 | 3.8 |
| 2 | 6.9 | 3.3 |
| 4 | 6.4 | 3.2 |

TABLE 10

Suppression of microbial growth

| Microorganism | Days after infection | $\log_{10}$ of No. of microorganism in liver | |
|---|---|---|---|
| | | control mice | Mice treated with peptide |
| E. coli | 3 | 6.1 | 3.3 |
| Ps. aeruginosa | 3 | 5.3 | 3.0 |
| C. albicans | 4 | 6.8 | 4.4 |

E. coli, Ps. aeruginosa, and C. albicans were infected intravenously with 5 × 10$^4$, 2.5 × 10$^4$, and 2 × 10$^3$, respectively. The peptide was pretreated daily for 10 times with 0.05 mg/kg/day by oral route.

TABLE 11

Protective activity against lethal infection by Candida and Pseudomonas

| Treatment | | Suppressive activity against lethal infection (survivals at day 15) | |
|---|---|---|---|
| | | C. albicans | Ps. aeruginosa |
| none | | 35/35 | 7/7 |
| 5-fluorouracil | 25 mg/kg/day × 10, i.p. | 5/35 | 2/7 |
| 5-fluorouracil + peptide | 25 mg/kg/day × 10, i.p. 0.05 mg/kg/day × 10, p.o. | 30/35 | 11/14 |
| + peptide | 0.005 mg/kg/day, × 10, p.o | 12/14 | 9/14 |

C. albicans and Ps. aeruginosa were infected intravenously with 1 × 10$^5$ and 4 × 10$^4$, respectively.

TABLE 12

Antimicrobial spectrum of the pentadecapeptide

| Test organisms | MIC (μg/ml) |
|---|---|
| E. coli NIHJ | >100 |
| E. coli NIHJ SMf | >100 |
| E. coli NIHJ STf | >100 |
| E. coli K-12 ML 1630 | >100 |
| E. coli CF17 | >100 |
| E. coli CF41 | >100 |
| Salmonella typhimurium IFO12529 | >100 |
| Salmonella schottmuelleri ATCC8759 | >100 |
| Citrobacter fraundii IFO12681 | >100 |
| Shigella flexneri ATCC25929 | >100 |
| Klebsiella pneumoniae PCI602 | >100 |
| Pseudomonas aeruginosa 6E313-3 | >100 |
| Pseudomonas aeruginosa A3 | >100 |
| Pseudomonas aeruginosa P2 | >100 |
| Proteus vulgaris OX19 ATCC6898 | >100 |
| Proteus vulgaris 5E78-1 | >100 |
| Bordetella bronchiseptica Aich 202 | >100 |
| Serratia marcescens IFO12648 | >100 |
| Staphylococcus aureus FDA209P | >100 |
| Staphylococcus aureus MS3937 | >100 |
| Staphylococcus aureus MS9261 | >100 |
| Staphylococcus aureus Smith | >100 |
| Bacillus subtilis PCI219 | 0.78 |
| Bacillus coagulans | >100 |
| Sarrcina lutea ATCC9341 | >100 |
| Candida albicans Yu1200 | >100 |
| Mycobacterium smegmatis ATCC607 | >100 |
| Listeria monocytogenes ATCC 15313 | >100 |

All results obtained strongly indicate that the pentadecapeptide is a promising material as an immunopotentiator.

The acute toxicity of the peptide is quite low and mice did not show any toxic symptoms when it was administered even at 1,000 mg/kg p.o. On the other hand, it is active against Bacillus subtilis as shown in Table 12.

The present peptide and salts thereof may accordingly be used as medicaments; for example, in the form of pharmaceutical preparations which contain them in association with a compatible pharmaceuticalcarrier material. This carrier material can be an organic or inorganic carrier material suitable for enteral (e.g. oral) or parenteral administration. Examples of such carrier materials are water, lactose, starch, magnesium stearate, gum arabic, gelatin, polyalkyleneglycols, petroleum jelly and the like. The pharmaceutical preparations can be made up in a solid form (e.g. as tablets, dragées, suppositories or capsules) or in a liquid form (e.g. as solutions, suspensions, emulsioms or ointments. The pharmaceutical preparations may be subjected to conventional pharmaceutical operations such as sterilisation and may contain adjuvants such as preservatives, stabilisers, wetting agents or salts for altering the osmotic pressure.

The pharmaceutical preparations can be prepared according to methods well known in the art.

They can be administered either orally or parenterally once a day up to four times a day. The oral dosage form may contain 0,1-100 mg, the parenteral dosage form 1 μg-10 mg of active ingredient.

The following examples illustrate the invention.

EXAMPLE 1

I. FERMENTATION

A nutrient medium was prepared from the following materials:

| | |
|---|---|
| Glucose | 10 g |

| -continued | |
|---|---|
| Soluble starch | 10 g |
| Soybean powder | 15 g |
| NaCl | 3 g |
| K₂HPO₄ | 1 g |
| MgSO₄.7H₂O | 1 g |
| Mineral stock solution* | 1 ml |
| Dionised water | 1 liter |

*The solution contains $MnCl_2.4H_2O$ (8 g), $CuSO_4.5H_2O$ (7 g), $ZnSO_4.7H_2O$ (2 g) and $FeSO_4.7H_2O$ (1 g) per liter of deionized water.

The pH of the above mixture was adjusted to 7 with 6N sodium hydroxide followed by steam sterilization at 120° C. for 20 minutes.

The scraped spores from an agar slant of Streptoverticillium griseoverticillatum subsp. NAR 164C-MY6 (FERM-P No. 4639) were used to inoculate ten 500-ml Erlenmeyer flasks containing 110 ml each of the above sterilized medium. The flasks were placed on a rotary shaker operating at 185 r.p.m. and agitated for 72 hours at 27° C. At the end of this time, the flask inocula were used to seed a 50-liter fermentor containing 25 liters of the same medium. The fermentation cycle was about 40 hours during which time the temperature was maintained at 27° C., filtered air was supplied at a rate of 25 liters per minute and agitation was at a rate of 600 r.p.m.

II. ISOLATION

(1) Adsorption on Amberlite IRC-50

The fermentation broth was centrifuged to remove the mycelium. A part of the supernatant (10 liters) was adjusted to pH 7.5 with 6N sodium hydroxide, and then passed through a column of Amberlite IRC-50 (H-form, 1 liter). The column was washed successively with water (10 liters) and 50% aqueous acetone (5 liters), and then eluted with a mixture of acetone and 0.5N hydrochloric acid (1:1, v/v). The active eluate was adjusted to about pH 5 with 6N sodium hydroxide and concentrated under reduced pressure to about 0.6 liter.

(2) Extraction with butanol

The aqueous concentrate (ca. 0.6 liter) was adjusted to pH 7.0 with dilute sodium hydroxide solution and then extracted with two 1.2 liter portions of n-butanol. The combined butanol extracts were washed with 10 ml of water and concentrated under reduced pressure to a small volume. Water was added, and the mixture was concentrated again under reduced pressure to ca. 1 liter.

(3) Chromatography on SP-Sephadex

The concentrate was passed through a column of SP-Sephadex C-25 (Na-form, 600 ml). The column was washed with 1 liter of 0.01 M sodium chloride and then eluted with a gradient between 1 liter each of 0.01 M NaCl and 0.05 M NaCl followed by elution with 0.05 M NaCl. The active eluate (2.2 liters) was concentrated under reduced pressure to about 600 ml.

(4) Desalting

The concentrate was adjusted to pH 4.0 with dilute HCl, and then passed through a column containing 60 ml of activated charcoal in water. The column was washed with water (300 ml) and eluted with 50% aqueous acetone. The eluate (ca. 2 liters) was concentrated under reduced pressure to an aqueous phase (20 ml). After the concentrate was allowed to stand at room temperature for 1 week, the precipitated crystalline material was collected by centrifugation, washed with small amounts of water and ethanol, and then dried over $P_2O_5$ under vacuum. There was obtained 480 mg of pure pentadecapeptide hydrochloride as white crystalline solid (m.p. 257°-259° C.).

EXAMPLE 2

In the fermentation procedure similar to the one described in Example 1, 22.5 liters of fermentation broth containing the pentadecapeptide were obtained. The broth was filtered with an aid of diatomaceous earth. The filtrate (pH 8.1) was passed through a column of Amberlite IRC-50 (H-form, 2 liters), and the column was washed successively with water (25 liters) and 50% aqueous acetone and then eluted with a mixture of acetone and 0.5N HCl (1:1, v/v). The active eluate (ca. 8 liters) was adjusted to about pH 6 with 6N NaOH and concentrated under reduced pressure to about 0.9 liter to give an aqueous suspension. The suspension was adjusted to pH 7.0 with dilute NaOH, and crude precipitated peptide was collected by centrifugation. To the precipitate was added water (1 liter), and the mixture was adjusted to pH 4.5 with dilute HCl. After stirring at room temperature for about 30 minutes, the mixture was centrifuged to remove a small amount of insoluble material. The supernatant was adjusted to pH 7.9 and then extracted with 1.6 liters of n-butanol, keeping the pH of the aqueous phase at 7.9 by addition of dilute NaOH. The butanol extract was concentrated under reduced pressure to give an aqueous suspension. Lyophilization of the suspension gave 5.48 g of the pentadecapeptide (95% purity) as a white powder, m.p. 240°-260° C. (dec.).

What is claimed:

1. A method of treating an immunologically supressed or deficient individual which comprises treating said individual with an immunopotentiating amount of a pharmaceutical composition consisting of a pentadecapeptide and salts thereof containing the following amino acids: arginine (1 mole), glutamic acid* (1 mole), lanthionine (1 mole), β-methyllanthionine (2 moles), D-phenylalanine (3 moles), glycine (2 moles), proline (1 mole), valine (1 mole), aspartic acid* (1 mole), β-hydroxyaspartic acid* (1 mole), and lysinoalanine (1 mole), the asterisks indicating that either two of these amino acids or one of them and the carboxy terminal amino acid are present as amides, the hydrochloride salt thereof being characterized by the following parameters:

(a) Melting point: 257°-259° C. (dec.);
(b) Specific rotation: $[\alpha]_D^{25} = -72°$ (C=1.0, 0.1N HCl);
(c) Ultraviolet absorption spectrum; Maxima at 251.5 nm-($E_1$ $_{cm}^{1\%}$=2.68), 257 nm($E_1$ $_{cm}^{1\%}$=2.90) and 263 nm-.) and a shoulder at 266 nm in water;
(d) Infrared absorption spectrum as shown in FIG. 2.
(e) Solubility in solvents: Soluble in water or methanol; hardly soluble in ethyl acetate; and insoluble in hexane;
(f) Color reaction: Positive to Sakaguchi and Reidon-Smith reactions, and negative to Pauly reaction;
(g) Thin layer chromatography on silica gel $F_{254}$ (Merck) in benzene/ethanol/25% aqueous ammonia (2:4:1, v/v/v): RF=0.4 in admixture with a pharmaceutical diluent or carrier.

2. The method of claim 1 wherein the oral dosage immunopotentiating amount of the pentadecapeptide or salts thereof is from about 0.1 mg to 100 mg and is administered from once a day to four times a day.

3. The method of claim 1 wherein the parenteral dosage immunopotentiating amount of the pentadecapeptide or salts thereof is from about 1 microgram to 10 mg and is administered from once a day to four times a day.

* * * * *